(12) United States Patent
Damadian et al.

(10) Patent No.: US 8,036,730 B1
(45) Date of Patent: Oct. 11, 2011

(54) TEMPORAL MAGNETIC RESONANCE IMAGING

(75) Inventors: Raymond V. Damadian, Woodbury, NY (US); Anthony J. Giambalvo, Kings Park, NY (US)

(73) Assignee: Fonar Corporation, Melville, NY (US)

( * ) Notice: Subject to any disclaimer, the term of this patent is extended or adjusted under 35 U.S.C. 154(b) by 2371 days.

(21) Appl. No.: 10/419,407

(22) Filed: Apr. 21, 2003

Related U.S. Application Data

(60) Provisional application No. 60/373,789, filed on Apr. 19, 2002.

(51) Int. Cl.
*A61B 5/05* (2006.01)
*G01V 3/00* (2006.01)

(52) U.S. Cl. ....................... 600/410; 324/307

(58) Field of Classification Search .......... 600/407–414; 324/307, 306, 309, 128, 130; 382/128, 130, 382/306–309
See application file for complete search history.

(56) References Cited

U.S. PATENT DOCUMENTS

| | | |
|---|---|---|
| 3,789,832 A | 2/1974 | Damadian |
| 4,350,998 A | 9/1982 | Verhoeven |
| 4,394,684 A | 7/1983 | Verhoeven |
| 4,411,270 A | 10/1983 | Damadian |
| 4,534,358 A | 8/1985 | Young |
| 4,608,991 A | 9/1986 | Rollwitz |
| 4,629,989 A | 12/1986 | Riehl et al. |
| 4,770,182 A | 9/1988 | Damadian et al. |
| 4,829,252 A | 5/1989 | Kaufman |
| 4,871,966 A | 10/1989 | Smith et al. |
| 4,875,485 A | 10/1989 | Matsutani |
| 4,908,844 A | 3/1990 | Hasegawa |
| 4,924,198 A | 5/1990 | Laskaris |
| 4,968,937 A | 11/1990 | Akgun |
| 4,985,678 A | 1/1991 | Gangarosa et al. |
| 5,008,624 A | 4/1991 | Yoshida |
| 5,065,761 A | 11/1991 | Pell |
| 5,153,546 A | 10/1992 | Laskaris |
| 5,162,768 A | 11/1992 | McDougall et al. |
| 5,197,474 A | 3/1993 | Englund et al. |
| 5,207,224 A | 5/1993 | Dickinson et al. |
| 5,250,901 A | 10/1993 | Kaufman et al. |
| 5,259,011 A | 11/1993 | Petro |

(Continued)

FOREIGN PATENT DOCUMENTS

JP     1-242056     9/1989

(Continued)

OTHER PUBLICATIONS

Damadian et al., U.S. Appl. No. 10/419,385, filed Apr. 21, 2003.

(Continued)

*Primary Examiner* — Unsu Jung
*Assistant Examiner* — Lawrence N Laryea
(74) *Attorney, Agent, or Firm* — Lerner, David, Littenberg, Krumholz & Mentlik, LLP

(57) ABSTRACT

A patient is subjected to magnetic resonance imaging at substantial intervals such as weeks, months or years, or after an interval sufficient for a therapeutic regimen to affect the anatomy, and the data acquired at different times is compared to show changes in the anatomy with time or due to the effects of the therapeutic regimen. Individual data elements or larger groups of plural data elements representing particular locations a set of image data acquired at one time can be automatically compared with data elements associated with the same locations in another set of image data acquired at another time to yield a set of comparison data.

31 Claims, 7 Drawing Sheets

U.S. PATENT DOCUMENTS

| | | | |
|---|---|---|---|
| 5,273,040 A | 12/1993 | Apicella et al. | |
| 5,289,374 A | 2/1994 | Doi et al. | |
| 5,305,365 A | 4/1994 | Coe | |
| 5,305,749 A | 4/1994 | Li et al. | |
| 5,315,248 A | 5/1994 | Yamaguchi | |
| 5,349,956 A | 9/1994 | Bonutti | |
| 5,386,447 A | 1/1995 | Siczek | |
| 5,436,607 A | 7/1995 | Chari et al. | |
| 5,490,513 A | 2/1996 | Damadian et al. | |
| 5,515,863 A | 5/1996 | Damadian | |
| 5,519,372 A | 5/1996 | Palkovich et al. | |
| 5,520,181 A | 5/1996 | Kreidler et al. | |
| 5,577,502 A * | 11/1996 | Darrow et al. | 600/426 |
| 5,592,090 A | 1/1997 | Pissanetzky | |
| 5,606,970 A | 3/1997 | Damadian | |
| 5,615,430 A | 4/1997 | Nambu et al. | |
| 5,640,958 A | 6/1997 | Bonutti | |
| 5,647,360 A | 7/1997 | Bani-Hashemi et al. | |
| 5,735,278 A | 4/1998 | Hoult et al. | |
| 5,743,264 A | 4/1998 | Bonutti | |
| 5,779,637 A | 7/1998 | Palkovich et al. | |
| 5,810,727 A | 9/1998 | Groen | |
| 5,873,824 A | 2/1999 | Doi et al. | |
| 5,878,746 A | 3/1999 | Lemelson et al. | |
| 5,997,883 A | 12/1999 | Epstein et al. | |
| 6,009,341 A | 12/1999 | Edelman | |
| 6,011,396 A | 1/2000 | Eckels et al. | |
| 6,023,165 A | 2/2000 | Damadian et al. | |
| 6,097,977 A | 8/2000 | Collick et al. | |
| 6,112,112 A | 8/2000 | Gilhuijs et al. | |
| 6,134,464 A | 10/2000 | Tan et al. | |
| 6,141,579 A | 10/2000 | Bonutti | |
| 6,198,957 B1 | 3/2001 | Green | |
| 6,241,671 B1 | 6/2001 | Ritter et al. | |
| 6,246,239 B1 | 6/2001 | Krogmann et al. | |
| 6,249,695 B1 | 6/2001 | Damadian | |
| 6,280,383 B1 * | 8/2001 | Damadian | 600/410 |
| 6,335,623 B1 | 1/2002 | Damadian et al. | |
| 6,411,088 B1 * | 6/2002 | Kuth et al. | 324/307 |
| 6,414,486 B1 | 7/2002 | Koellner et al. | |
| 6,414,490 B1 | 7/2002 | Damadian et al. | |
| 6,509,735 B2 | 1/2003 | Mueller et al. | |
| 6,534,982 B1 | 3/2003 | Jakab | |
| 6,541,973 B1 | 4/2003 | Danby et al. | |
| 6,556,008 B2 * | 4/2003 | Thesen | 324/307 |
| 6,559,641 B2 | 5/2003 | Thesen | |
| 6,567,684 B1 * | 5/2003 | Chenevert et al. | 600/410 |
| 6,586,934 B2 | 7/2003 | Biglieri et al. | |
| 6,667,618 B2 | 12/2003 | Thesen | |
| 6,677,753 B1 * | 1/2004 | Danby et al. | 324/318 |
| 6,690,962 B2 * | 2/2004 | Schmitz et al. | 600/420 |
| 6,725,078 B2 | 4/2004 | Bucholz et al. | |
| 6,828,792 B1 | 12/2004 | Danby et al. | |
| 6,844,884 B2 | 1/2005 | Balloni et al. | |
| 6,909,792 B1 * | 6/2005 | Carrott et al. | 382/128 |
| 6,975,896 B2 * | 12/2005 | Ehnholm et al. | 600/414 |
| 7,020,578 B2 * | 3/2006 | Sorensen et al. | 702/181 |
| 7,151,816 B2 | 12/2006 | Maier et al. | |
| 7,239,906 B1 | 7/2007 | Green et al. | |
| 7,375,521 B1 | 5/2008 | Damadian et al. | |
| 2003/0009098 A1 * | 1/2003 | Jack et al. | |
| 2003/0016850 A1 * | 1/2003 | Kaufman et al. | 382/128 |
| 2003/0055331 A1 * | 3/2003 | Kotmel et al. | 600/410 |
| 2005/0187459 A1 | 8/2005 | Trequattrini et al. | |

FOREIGN PATENT DOCUMENTS

JP      H01-242056      9/1989

OTHER PUBLICATIONS

Damadian, U.S. Appl. No. 10/200,943, filed Jul. 23, 2002.
Danby et al., U.S. Appl. No. 09/718,946, filed Nov. 22, 2000.
Official Action, mailed Jun. 18, 2003, in U.S. Appl. No. 10/200,943.

* cited by examiner

TEMPORAL MAGNETIC RESONANCE IMAGING

CROSS-REFERENCE TO RELATED APPLICATIONS

The present application claims benefit of U.S. Provisional Patent Application Ser. No. 60/373,789, filed Apr. 19, 2002, the entire disclosure of which is hereby incorporated by reference herein.

BACKGROUND OF THE INVENTION

The present invention relates to imaging techniques and apparatus for performing such techniques.

In magnetic resonance imaging ("MRI"), a strong, uniform magnetic field is applied to the region of the patient to be imaged. Radio frequency ("RF") energy is applied to this region of the patient by a transmitter and antenna. The RF energy excites atomic nuclei within the patient's tissues. The excited nuclei spin at a rate dependent upon the magnetic field. As they spin, they emit faint RF signals, referred to herein as magnetic resonance signals. By applying small magnetic field gradients so that the magnitude of the magnetic field varies with location within the patient's body, the magnetic resonance phenomenon can be limited to only a particular region or "slice" of the patient's body, so that all of the magnetic resonance signals come from that slice. Moreover, by applying additional magnetic field gradients, the frequency and phase of the magnetic resonance signals from different locations within the slice can be made to vary in a predictable manner depending upon the position within the slice. Stated another way, the magnetic resonance signals are "spatially encoded," so that it is possible to distinguish between signals from different parts of a slice.

If this process is repeated numerous times to elicit signals using different gradients, it is possible to derive a set of information which indicates one or more characteristics of magnetic resonance signals from particular locations within the patient's body. Such a set of information is referred herein to as an image data set. Because the characteristics of the magnetic resonance signals vary with the concentration of different chemical substances and other chemical characteristics of the tissues, different tissues provide different magnetic resonance signal characteristics. When a magnetic resonance signal image data set is displayed in a visual format, such as on a computer screen or printed image, the information forms a picture of the structures within the patient's body, with different tissues having different intensities or colors.

Typically, a magnetic resonance image data set is stored as a set of individual data elements. The data in each element represents one or more characteristics of magnetic resonance signals from a small volume element or "voxel." For example, the map can be stored as a three-dimensional array of data elements, the dimensions of the array corresponding to three-dimensional space. Data elements corresponding to a given plane in three-dimensional space can be selected for display in a two-dimensional picture such as a screen display or printed image. Each small area element on the surface of the picture, commonly referred to as a "pixel," is assigned an intensity or color value based on the numerical values of the data element for the corresponding voxel.

MRI has been widely adopted in the medical arts. Because MRI does not use X-rays or other ionizing radiation, it offers safety advantages over techniques such as conventional X-ray imaging, fluoroscopy and CAT imaging.

Moreover, MRI allows visualization of tissues which are difficult or impossible to depict using other techniques. Magnetic resonance imaging can show abnormal tissues in contrast to surrounding normal tissues. For example, as disclosed in U.S. Pat. No. 3,789,832 of Raymond V. Damadian, magnetic resonance signals from malignant tumors have a characteristic referred to as the spin-lattice relaxation time or "$T_1$" different from the $T_1$ of normal tissues. If a magnetic resonance image is taken so that the data in each data element depends at least in part on the $T_1$ of the tissue at the corresponding location, a picture showing malignant tumor tissue in contrast to normal tissue can be displayed.

MRI is also particularly useful in imaging the spine. MRI can depict the vertebrae in conjunction with related tissues such as the lamina or "discs," as well as nerves, muscles and other neighboring tissues.

In magnetic resonance angiography, the magnetic field gradients applied during imaging, and the characteristics of the magnetic resonance signals which are translated into the image, are selected according to principles well-known in the art so that the data in voxels within arteries differs from the data for voxels in other structures, so that the arteries can be depicted in contrasting color or density to surrounding tissues. For example, arterial blood has a significant velocity and the surrounding tissues are nearly stationary. A so-called "motion-sensitive" MRI technique can be used so that a characteristic of the magnetic resonance signals from each voxel depends on the velocity of matter within the voxel. Magnetic resonance angiography yields images directly analogous to those obtained by conventional angiography, without the need for X-ray exposure. In some cases, MRI angiography can be performed without injection of a contrast medium. Moreover, MRI angiography can provide three-dimensional imaging information, so that images from any desired perspective can be displayed.

However, magnetic resonance imaging procedures have suffered from significant limitations. Conventional MRI equipment requires the patient in a supine position on a horizontal bed which fits with the patient receiving space of the static field magnet. Some medical conditions have effects which change with posture. For example, a spinal disc may impinge on a nerve or other surrounding structure only when the patient is in an upright posture so that the disk is compressed by the patient's weight. Various proposals have been advanced to allow MRI procedures to be performed on patients in a posture other than the conventional supplying of posture. For example, Japanese published Patent Application No. 1-242056 published Sep. 27, 1989 depicts a magnetic resonance imaging unit with a tilting bed for supporting the patient in a supine position or in a standing position. Yoshida, U.S. Pat. No. 5,008,624 depicts a magnetic resonance imaging instrument with movable static field magnet in conjunction with a patient carrier which supports the patient in "various postures." Palkovich et al., U.S. Pat. No. 5,779,637 discloses a system in which the patient lies supine within the static field magnet during one imaging procedure. The entire system, including the static field magnet and the patient can be pivoted so as to swing the magnet, the patient bed and the patient as a unit to a different position in which the patient bed extends vertically and the patient in an upright posture. A further image is taken in this position. None of these systems have been widely adopted.

Copending, commonly assigned U.S. patent application Ser. No. 09/718,946, filed Nov. 22, 2000 ("the '946 application"), now U.S. Pat. No. 6,677,753, the disclosure of which is hereby incorporated by reference herein and copending commonly assigned U.S. patent application Ser. No. 09/789, 460 ("the '460 application"), now U.S. Pat. No. 6,414,490, the disclosure of which is also incorporated by reference herein, describe additional MRI magnet structures and patient handling devices as well as additional imaging methods. As disclosed for example in certain embodiments of the '946 application, a patient support such as a bed which can both tilt and elevate can be used in conjunction with a static field magnet to allow imaging of a patient in various orientations and to position various portions of the patient's anatomy in the appropriate location relative to the magnet for imaging. Discussion of the '946 and '460 applications in this background section of the present application should not be taken as an admission that the same constitute legally available prior art with respect to the present invention.

Most commonly, pictures derived from MRI images are read by a physician visually examining the picture to diagnose disease which may be present or to evaluate the progress of a known disease. Such evaluation may involve, for example, a mental comparison by the physician with his or her memory of pictures the physician has previously seen of normal and other diseased patients or pictures taken in the past of the same patient. This task requires careful examination and considerable professional judgment. Even with the capabilities achievable in MRI imaging, it is not always easy to spot disease states or changes in the patient's condition. Lemelson et al., U.S. Pat. No. 5,878,746 proposes an automated process in which the computer examines a new image to extract "features relating to particular disease states" using a pattern recognition technique and stores signals descriptive of these features in a "fact database." These "feature signals" are compared with similar "feature signals" extracted from previously acquired images and the resulting comparison information is subjected to artificial intelligence rules to provide "a diagnostic assessment." Perhaps because of the extraordinary difficulty of developing appropriate automated tools for finding features relating to disease states and rules for deriving diagnostic assessments from the compared features, this approach has not been adopted widely, if at all, in practice. Thus, the physician still generally faces the task of visually observing a picture of a patient derived from a particular MRI imaging session and mentally comparing that picture with either a prior picture of the same patient or a mental image of a "normal" anatomy. In this process, the physician typically attempts to discern the outlines of body structures in the picture.

As disclosed in Apicella et al., U.S. Pat. No. 5,273,040, the volume of blood contained within the ventricles of the heart can be determined from an MRI image. To do this, the physician, or an automated system must accurately identify the boundary of the blood-containing ventricle. To enhance the accuracy of an automated process for detecting where the boundary lies, two MRI images taken through the patient's heart in rapid succession, as, for example, during successive heartbeats, are mathematically superimposed and subtracted from one another to yield a "difference image." Because the two MRI images are taken at two slightly different points in the cardiac cycle, the ventricles will be of slightly different sizes in the two images. Subtraction of the images will eliminate essentially all of the data, leaving only a small border or line having a width corresponding to the change in size between the first and second images. The difference image thus provides a clear line indicating the border of the ventricle which can be recognized in an automated system.

As disclosed in Bani-Hashemi et al., U.S. Pat. No. 5,647,360, digital subtraction angiography or "DSA" typically is performed using a computerized tomography or "CT" x-ray scan. A first set of CT scan data is obtained before injection of a contrast agent into the blood vessels, whereas a second scan is obtained a few minutes later, after injection of the contrast agent. The two data sets are registered with one another and subtracted from one another to yield a difference image which shows the blood vessels in high contrast. The registration procedure used to correlate data elements at corresponding locations within the patient in the two images with one another for subtraction operates by applying a mathematical transformation to one or another of the data sets. Different transformations are used for different parts of the transformed image so as to compensate for warping or non-uniform motion of different parts of the patient. The transformation for each portion of the image is determined using a pattern recognition procedure to match corresponding features shown in each portion of the image with corresponding features shown in the other image. The Bani-Hashemi patent suggests briefly that the registration technique "can be useful in various imaging systems, such as CT, MRI, PET, etc."

Despite all of the effort devoted in the art heretofore to development of imaging systems and techniques, still further enhancements would be desirable.

SUMMARY OF THE INVENTION

One aspect of the invention provides methods of monitoring changes in the body of a patient over time. A method according to this aspect of the invention desirably includes the steps of imaging a part of a patient by magnetic resonance in a first imaging step at a first time so as to provide a first image data set, and imaging at least that part of the patient by magnetic resonance in a second imaging step at a later time. The method desirably includes the step of comparing the two image data sets so as to detect a non-cyclical change in the patient's anatomy, i.e., a change other than a temporary deformation of anatomical structures caused by the cardiac or respiratory cycles. For example, methods according to this aspect of the invention can detect changes due to response to a therapeutic agent or the progression or regression of disease over time. The second imaging step optionally may be performed days, weeks or months later than the first imaging step.

The first and second data may be provided in a common frame of reference and compared by computer so as to provide a comparison image data set. The method desirably includes the step of displaying a visually perceptible image based at least in part on the comparison image data set. For example, the displaying step may include the step of automatically highlighting portions of the visually perceptible image representing at least some regions of the body where the comparison image data set indicates the presence of differences between the first and second image data set. The preferred methods according to this aspect of the present invention can greatly simplify the task of the physician in spotting changes in anatomy over time as, for example, the growth of abnormal tissue. According to a further aspect of the invention, at least one of the magnetic resonance imaging steps is performed so as to acquire data, referred to herein as "tissue data" indicative of the presence or absence of a predetermined characteristic in a body tissue. The predetermined characteristic may be, for example, an abnormal characteristic or a characteristic of a particular tissue type. For example, the magnetic resonance signal characteristics incorporated in the first or second image data sets may include characteristics such as $T_1$ indicative of malignancy. The highlighting step may be performed so as to highlight those portions of the visually perceptible image which represent at least some of the regions of the body where two conditions apply: first, that the tissue data indicates the presence of the predetermined characteristic and second, that the difference data set indicates the presence of differences. In this approach, the displayed image combines the results of two techniques which help to isolate regions of interest for further study.

Preferably, each of the first and second image data sets includes data elements each having coordinates. The data in each data element of each data set represents at least one characteristic of magnetic resonance signals from tissue at a physical location in a frame of reference associated with that data set, such physical location being specified by the coordinates. The method may further include the step of specifying a particular anatomical structure and the comparing step may include registering the first and second data sets with one another in a common frame of reference so that first data elements representing the specified anatomical structure in the first image data set have the same coordinates, in the common frame of reference, as second data elements representing the specified anatomical structure in the second data set.

The comparing step desirably includes comparing the data in one or more groups of first elements with the data in one or more groups of second elements having the same coordinates in the common frame of reference. Each group of data elements may include a single data element having data representing properties of magnetic resonance signals from a single volume element. For example, where each group includes a single data element, the data in a first data element may be subtracted from the data in a second data element having the same coordinates in the common frame of reference, or vice-versa. Other types of comparison, such as division or a determination as to equality or inequality between the data in these elements, may be used. In the alternative, each group of data elements may include a plurality of data elements having data representing properties of magnetic resonance signals from a plurality of contiguous volume elements or from a plurality of non-contiguous volume elements. Where each group of data elements includes a plurality of data elements, a composite property of the group, such as the sum or mean of the data in the various data elements in the group or a measure of variance among the data in the various data elements such as the standard deviation can be determined. In this case, the step of comparing the data in first and second groups of data elements may be performed by comparing the composite properties of these groups to one another.

As further discussed below, it is relatively simple to register the data sets at a particular, readily identifiable anatomical structure. If the data sets are registered at a particular anatomical structure, the comparison image set will accurately reflect meaningful anatomical changes in the vicinity of that anatomical structure.

These and other aspects, features and advantages of the present invention will be more readily apparent from the detailed description of the preferred embodiments set forth below, taken in conjunction with the accompanying drawings.

DETAILED DESCRIPTION OF THE PREFERRED EMBODIMENTS

Figure 1:
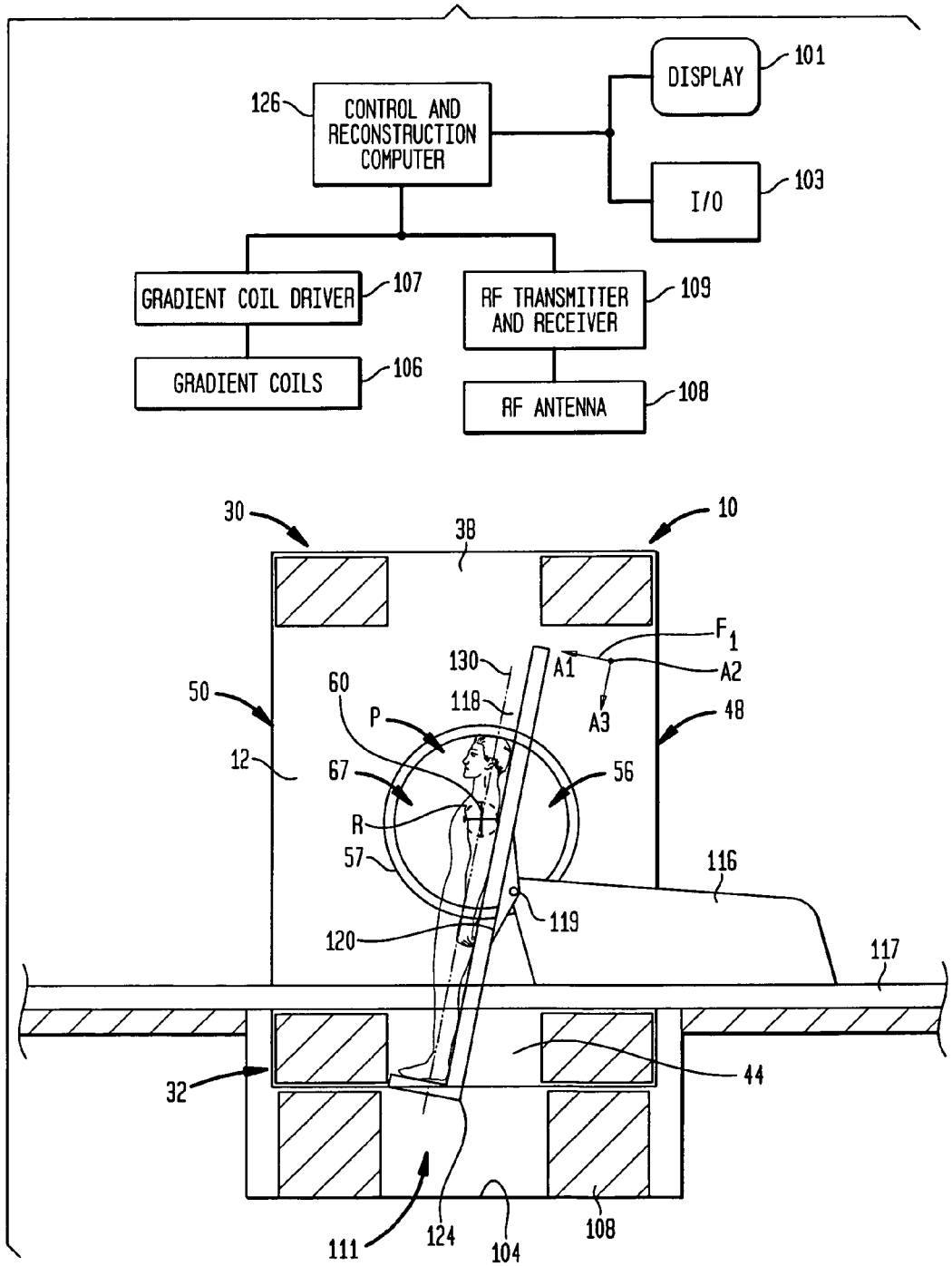
FIG. 1 is a diagrammatic sectional view of apparatus used in a method according to one embodiment of the invention during one step of the method.
Figure 2:
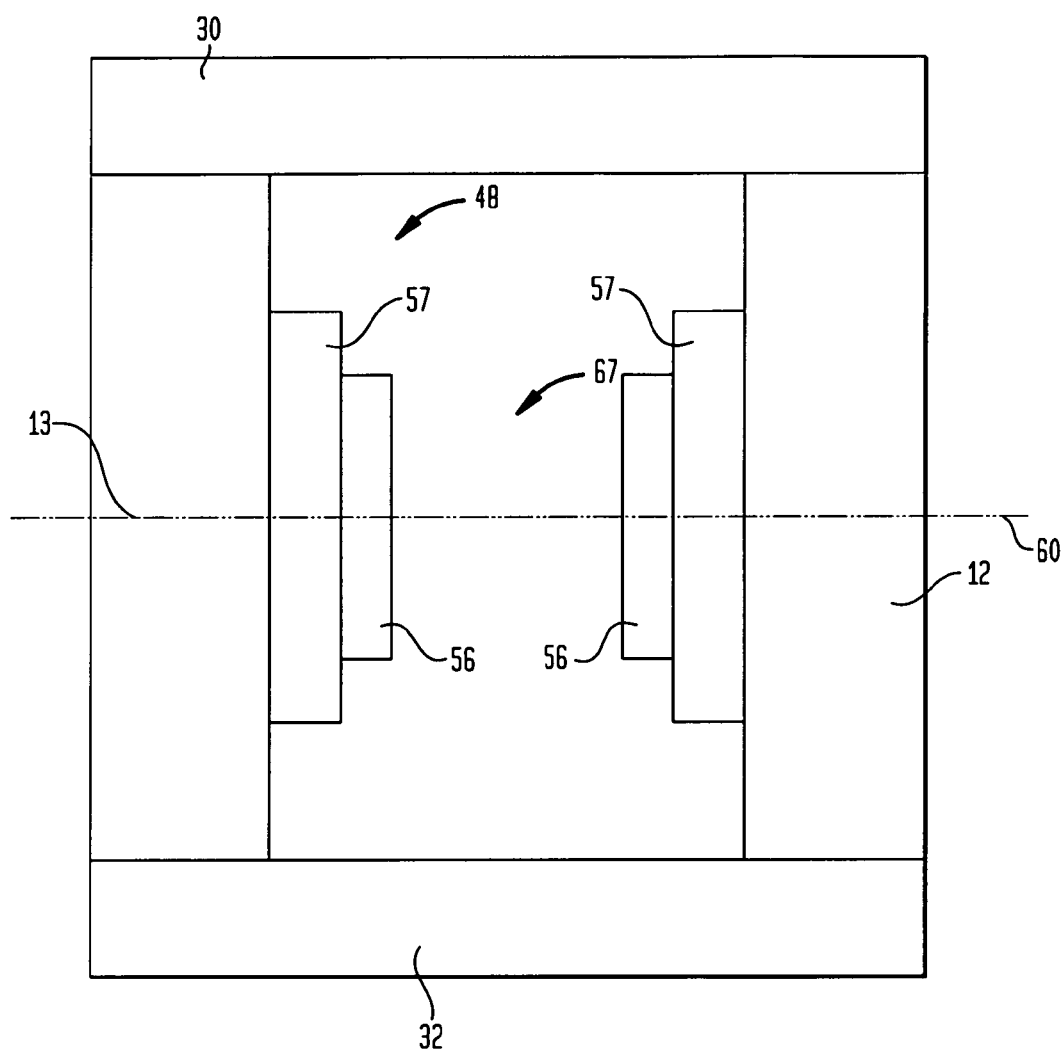
FIG. 2 is a diagrammatic end elevational view depicting part of the apparatus shown in FIG. 1.

Although many different types of magnetic resonance imaging apparatus can be used in accordance with the present invention, one apparatus used in one embodiment of the present invention is depicted in FIG. 1. This apparatus includes a ferromagnetic frame 10. As described in greater detail in the '946 application, the frame 10 is generally in the form of a hollow rectangular solid and includes a top flux return member 30 defining the top wall of the frame, a bottom flux return member 32 defining the bottom wall of the frame and a pair of generally vertical side walls 12 and 13 (FIG. 2) defining the sides of the frame, one such side wall 12 being visible in FIG. 1. The frame has large patient entry openings 48 and 50 (FIG. 1) at front and back sides of the frame, i.e., the vertical sides which are not occupied by side wall 12 and the opposite side wall. The top flux return member 30 defines opening 38 in the top wall of the frame, whereas the bottom flux return member 32 defines an opening 44 in the bottom wall. The frame-like structure is maintained above a base structure 104 so that there is a space 111 beneath the bottom of the flux return member communicating with opening 44.

Two cylindrical ferromagnetic poles 56, extend into the interior of the frame from side walls 12 and 13. The poles extend on a common horizontal polar axis 60 and define a patient receiving space 67 between them. The apparatus also includes a source of magnetic flux such as electromagnet coils 57 encircling the poles for providing a constant, substantially uniform static magnetic field within patient-receiving space 67.

A carriage 116 has a patient positioning assembly mounted thereon. The patient positioning assembly includes an elongated elevator frame pivotally mounted to the carriage for movement about a horizontal pivot axis 119. The patient positioning assembly further includes an elongated patient support or bed 120 with a footrest 124 at one end. The patient support is slidably mounted on the carriage. Appropriate actuators (not shown) are provided for driving the carriage along rails 117; for moving the patient support along the elevator frame 118 and for tilting the elevator frame about axis 119 relative to the carriage, so as to position patient support 120 in a generally vertical orientation as seen in FIG. 1.

A set of gradient coils 106 is physically mounted within the magnet frame. The gradient coils are arranged in the conventional manner to apply magnetic field gradients within the patient-receiving space. The gradient coils in turn are connected to a gradient coil driver 107 which is controlled by computer 126. In the conventional manner, the computer 126 can control the gradient coil driver to apply appropriate currents to the various gradient coils so as to provide gradients in the desired direction within patient-receiving space 67 and to vary these gradients with time.

A conventional RF antenna 108 and RF transmitting and receiving apparatus 109 are also associated with the control and reconstruction computer 126. The antenna may include one or more elements positioned in the conventional manner within the magnetic frame, on the patient support 120 or even carried by the patient. The transmitting and receiving apparatus can be actuated by the computer to apply RF excitation signals and to receive the magnetic resonance signals emitted by the patient. The apparatus may use the same or different antenna elements for transmitting and receiving.

The apparatus further includes a system controller, also referred to as a control and reconstruction computer 126, linked to a display 101 such as a CRT display or printer and input/output devices 103 for entry of data and control commands into the computer. The control and reconstruction computer includes the conventional elements of a general-purpose computer, including a programmable processor and conventional memory devices for storing data and programs. The input/output devices 103 may include conventional elements such as a keyboard, as well as a conventional pointing device such as a mouse, touchpad or trackball, and may also include specialized command entry devices such as switches or pushbuttons used to control at least some aspects of movement of patient support 120. The system controller or computer 126 is linked through an interface (not shown) to the patient positioning assembly 116, so that the computer can control positioning of patient support 120. The positioning arrangement is further described in the aforementioned U.S. Provisional Patent Application Ser. No. 60/373,789 ("the '789 provisional application") and in the commonly assigned, co-pending non-provisional U.S. patent application entitled POSITIONAL MAGNETIC RESONANCE IMAGING" filed of even date herewith and claiming benefit of said '789 provisional application. The disclosure of such non-provisional application is incorporated by reference herein.

In a method according to one embodiment of the invention, a patient P is disposed on patient support 120 so that the patient's back rests against the support and the patient's feet rest on footrest 124. To facilitate loading, the system may command the actuator to move the patient support to a pre-selected loading position (not shown) in which the patient support is generally vertical with footrest 124 near the level of the surrounding floor and rails 117, so that the patient can readily walk across the floor and step onto the footrest. This provides an easy and non-threatening loading procedure for ambulatory patients. Preferably, in the loading position the patient support is tilted back so that the plane of the support is at an angle of about 5-10 degrees from vertical. Thus, when the patient is positioned on the support, gravity will tend to hold the patient's back against the support.

When the patient is loaded on the support and the support and patient are in the desired position shown in FIG. 1, the operator enters a command through input-output devices 103 to commence imaging. In the particular position depicted in FIG. 1, the patient P is in a substantially erect orientation, with the long or head-to-toe axis 130 of the patient extending substantially vertical as, for example, within 15 degrees of vertical, more desirably within 10 degrees of vertical and most preferably within 5 degrees of vertical. Also, in this position a region R of the patient, indicated by a broken line circle in FIG. 1 is disposed in alignment with the polar axis 60 within the patient-receiving space 67, so that this region can be imaged.

While the patient P is positioned as shown in FIG. 1, the apparatus is actuated to obtain a magnetic resonance image referred to herein as a "scout" image of structures within region R. In the MRI imaging procedure, magnetic field gradients within space 67 are applied by the gradient coils along three orthogonal axes $A_1$, $A_2$, $A_3$, which cooperatively constitute a first frame of reference $F_1$. The applied gradients are referred to as the slice select, readout and phase encoding gradients. As discussed below, the scout image can be used to select positions and orientations of slices imaged for diagnostic purposes, referred to herein as "operative" slices. The magnet is capable of applying field gradients along arbitrary axes at any orientation relative to the physical structures of the magnet. The orientation of axes $A_1$, $A_2$ and $A_3$ and the assignment of gradients to particular axes are selected so that the information obtained will permit reconstruction of a scout image in a plane which is normal to or nearly normal to the planes of the images which are desired for diagnostic purposes. In the particular situation shown in FIG. 1, axis $A_1$ is aligned with the anterior-to-posterior axis of the patient, axis $A_3$ is aligned with the longitudinal axis of the patient and axis $A_2$ (projecting out of the plane of the drawing) is aligned with the lateral axis of the patient. In the first scout imaging sequence, the slice select gradient is applied on axis $A_1$, whereas the readout or frequency-encoding gradient is applied on one of remaining axes $A_2$ and $A_3$ and the phase-encoding gradient is applied on the other one of these axes.

Figure 3:
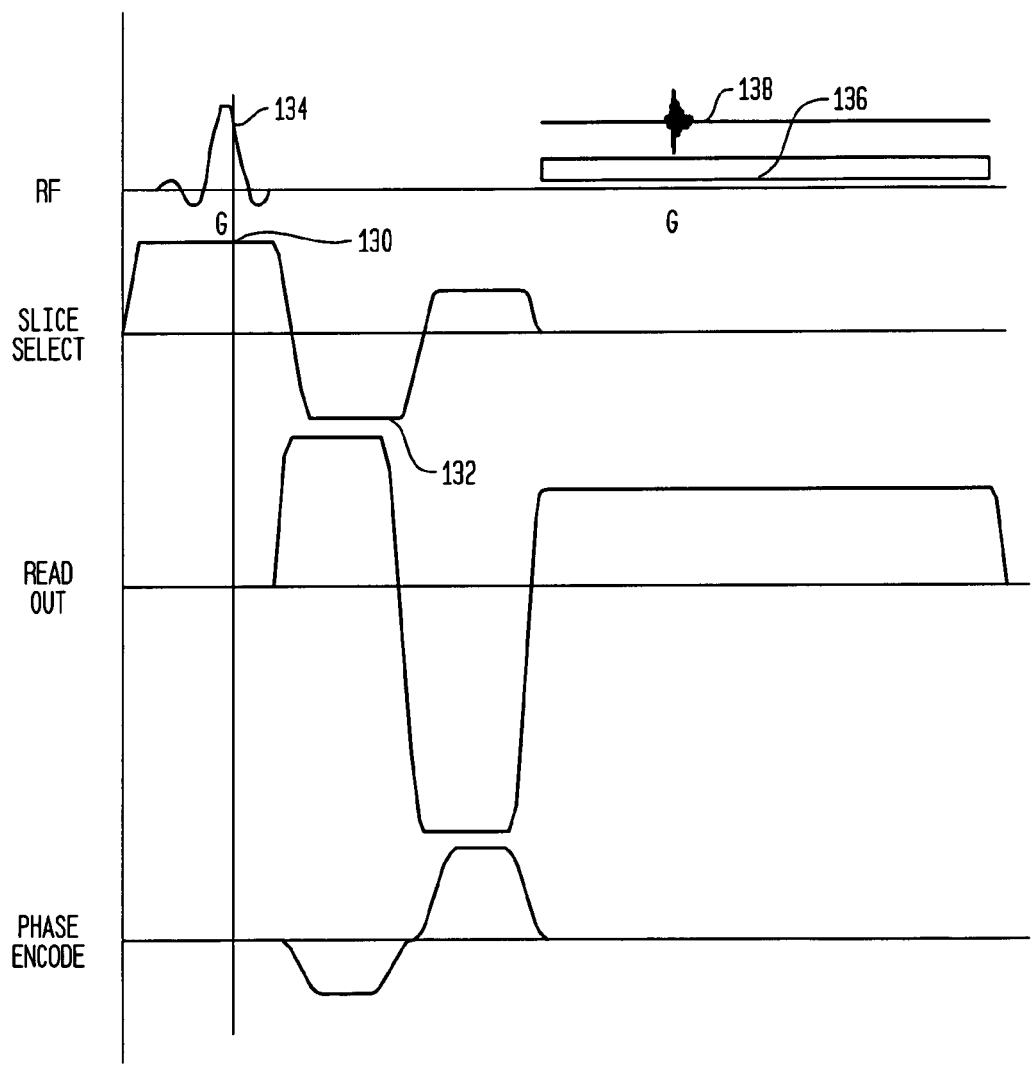
FIG. 3 is a diagrammatic MRI pulse sequence diagram used in the method of FIG. 1.

The gradients along the different axes vary with time in a pre-selected manner. One or more RF excitation pulses are applied by the RF transmitter. The cycle of operations required to elicit a single set of RF signals from the patient is commonly referred to as a "pulse sequence." One example of a pulse sequence is shown in FIG. 3. The gradients along the three axes are separately plotted against time in FIG. 3. In each plot, distance above or below the horizontal axis of the plot represents the magnitude of the gradient. The sign of the gradient is shown by whether the plot lies above or below the axis. For example, the magnetic field gradient along the slice select axis within the patient-receiving space is in a first, positive direction during the interval represented by plot segment 130. During a later interval represented by segment 132, the gradient along the slice select axis is in the opposite, negative direction. The particular sequence of gradients is merely illustrative; any pulse sequence can be used.

During application of the slice select gradient, a pulse of RF energy is applied as indicated schematically at 134. The RF energy excites nuclei within a slice of tissue transverse to the slice select axis. The receiver in unit 109 is operated to receive magnetic resonance signals from the tissue during a so-called receive window or interval indicated schematically by an elongated bar 136 in FIG. 3. Under the influence of the various gradients, the nuclei within the selected slice of tissue emit RF signals schematically indicated at 138 in FIG. 3. These signals are "spatially encoded." That is, signals from different volume elements or "voxels" at different locations within the selected slice have different phases and frequencies. In the conventional manner, the cycle of operations or pulse sequence shown in FIG. 3 is repeated many times using different gradient patterns as, for example, different phase encoding gradient magnitudes in different repetitions. In the example shown in FIG. 1, the slice selection gradient direction SS, along axis $A_1$, is directed substantially perpendicular to the plane of the patient support 118 and hence substantially perpendicular to a coronal plane of the patient's body, whereas the phase encoding gradient PE, along axis $A_3$, is perpendicular to the slice selection gradient direction and parallel to the coronal plane. The frequency encoding gradient direction, along axis $A_2$, is perpendicular to the slice select axis $A_1$ and to the phase encoding axis $A_3$, and is parallel to the coronal plane of the patient.

The magnetic resonance signals 138 received during the various repetitions of the cycle are digitized and stored in a memory (not shown) incorporated in the control and reconstruction computer 126. Using conventional techniques, these digitized signals are processed mathematically so as to recover information from the signals for individual voxels within the selected slice. The information recovered thus provides an array of data elements, each such data element having coordinates along the $A_1$, $A_2$ and $A_3$ axes of the first frame of reference $F_1$ defining the location of the voxel in that frame of reference and also having data defining one or more parameters related to the chemical composition and physical state of the matter within the voxel. The computer 126 reconstructs the data constituting the first, or coronal scout image into a visible image $SC_{1C}$ (FIG. 4), which is displayed on monitor 101.

Figure 5:
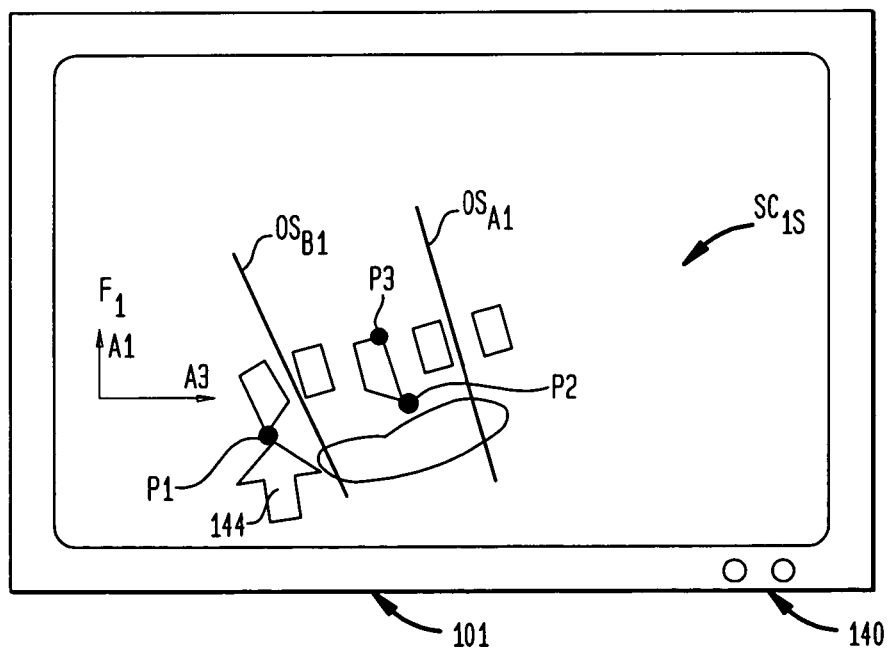

In exactly the same manner, the control computer acquires another scout image data set in the same frame of reference $F_1$ but defining an additional scout slice in a plane normal to the plane of the first scout slice. In this process, the slice select gradient may be directed along axis $A_2$, into and out of the plane of the drawing in FIG. 1, whereas the phase encoding and readout gradients may be directed along axes $A_1$ and $A_3$, so that the acquired data defines a scout image $SC_{1S}$ in a sagital plane, which also may be reconstructed and displayed on monitor 101 as seen in FIG. 5.

Figure 4:
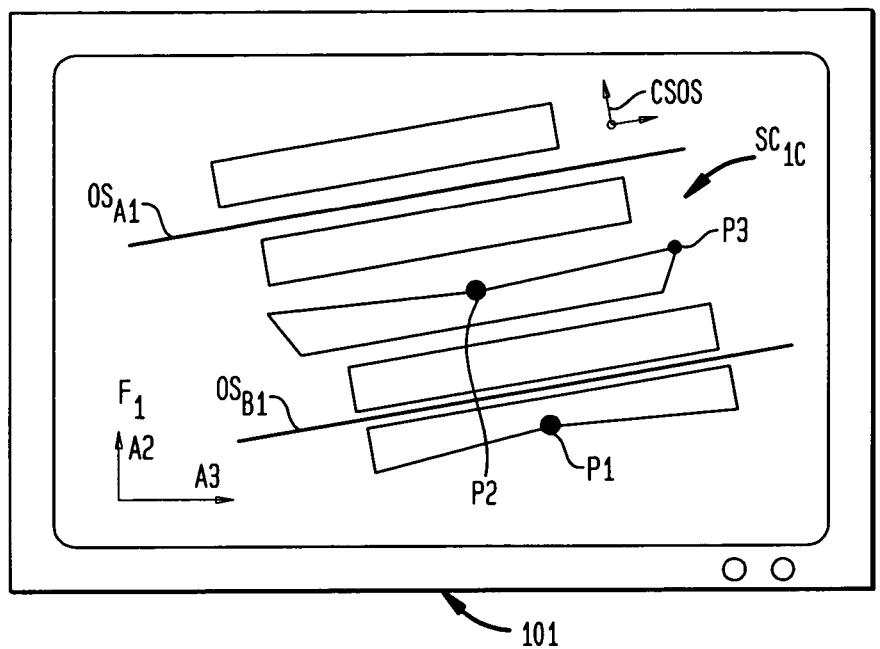
FIGS. 4 through 9, inclusive, are simplified, diagrammatic views of images displayed during the method of FIGS. 1-3.

One or both of the scout images can be used in the conventional manner to select and specify the planes for one or more slices, typically many slices, useful in evaluation of anatomical structures, referred to herein as the "operative" slices. For example, the operator may command the control computer to display a line or plane representing the orientation and position of a proposed slice on monitor 101 in conjunction with either scout image $SC_{1C}$ or $SC_{1S}$. Using controls 140 associated with the monitor and linked to the control computer, the operator instructs the computer to reorient or move the slice. The computer moves the line or plane representation of the slice on the image to represent the moved position and orientation. The operator continues this process until the representation of the slice is in the desired relationship to the anatomical structures of the patient as shown on the scout image. For example, in FIGS. 4 and 5, the operator has caused the computer to position representations of two proposed operative slices $OS_{A1}$ and $OS_{B1}$, laid on scout images $SC_{1C}$ and $SC_{1S}$. Although only two operative slices are illustrated in FIGS. 4 and 5, any number of operative slices may be acquired. Also, the operative slices all may lie at the same orientation or may have differing orientations.

Once the operator is satisfied with the disposition of the proposed slices relative to the patient, the operator signals the computer to acquire imaging data in the slices. The computer applies a slice selection gradient in a direction normal to the plane of each proposed slice and readout and phase encoding gradients in directions within that plane and applies RF signals in the manner discussed above with reference to acquisition of the scout images. In the same manner as discussed above, the system acquires magnet resonance data for voxels lying within each operative slice. The positions and orientations of the operative slices are known in the first frame of reference F1. Stated another way, position in a coordinate system $CS_{OS}$ (FIG. 4) having axes in the plane of a particular operative slice or normal to such plane has a fixed, known relationship to position in coordinate system $A_1, A_2, A_3$ of the scout image. Here again, the data for the operative slices includes data defining the location of the voxel in the coordinate system of the operative slice and, hence, in the first frame of reference $F_1$, and data defining one or more parameters relating to the chemical composition and physical state of the matter within the voxel. This data constitutes a first image data set. Data defining the scout images is recorded in a similar manner. Also, data defining the position and orientation of each slice in the scout image coordinate system, and the orientations of the gradients used to image each slice is recorded either explicitly or implicitly. Providing that the data defining the relationship between the coordinate system of the operative slices and the coordinate system of the scout slices is recorded, it is immaterial whether data for individual voxels of the operative slices are recorded in the scout image coordinate system $CS_{OS}$ or in the operative slice coordinate system $A_1, A_2, A_3$. The data defining the operative slices, of course, may be reconstructed as newly perceptible images and reviewed by a physician in the conventional manner. The data elements may be recorded in any form within a computer memory. For example, the coordinates and data may be recorded explicitly as a set of multiple numerical values for each data element. Alternatively, the data elements can be stored as an ordered array of values in memory, with the coordinates of each data element being implicit in the location of such data element in memory. In that embodiment, only the data values are stored as explicit numerical values. The recorded data may also include data defining the orientation of the patient relative to gravity as, for example, the tilt angle of the table holding the patient.

In the next stage of the method, the patient is imaged again at a later time to acquire a second image data set. Preferably, the patient is positioned in the apparatus in the same orientation relative to gravity as was used during acquisition of the first data set. In exactly the same manner as discussed above, scout images $SC_{2C}$ and $SC_{2S}$ are acquired. Preferably, the second scout images are generally similar to the first scout images, i.e., if the first scout images were sagital and coronal images, then the second scout images also should be sagital and coronal images. However, the frame of reference $F_2$ of the second scout images, indicated by coordinate system $B_1, B_2, B_3$, is not in precisely the same relationship to the patient's body as the frame of references of the first scout images, inasmuch as the patient may not be in exactly the same position relative to the apparatus during acquisition of the second scout images.

In the next stage of operation, the operator instructs the computer to display the coronal second scout $SC_{2C}$ image on display unit 101 and also to display a cursor 144 overlayed on the images. Using controls 140, the operator maneuvers the cursor on the monitor until the cursor is aligned with a well-defined point $P_1$, referred to herein as a "fiducial point," as, for example, the tip of the sternum or other structure having a well defined, readily identifiable shape. Once the cursor is aligned, the operator enters a signal indicating such alignment. The computer records the current position of the cursor as coordinates along axes $B_2$ and $B_3$ of the second frame of reference. In a similar fashion, the operator aligns the cursor with other points $P_2$ and $P_3$ in the coronal scout image $SC_{2C}$ so as to provide coordinates for all of points $P_1, P_2$ and $P_3$ along axes $B_2$ and $B_3$. The operator then commands the computer to display the sagital second scout image $SC_{2S}$ and maneuvers the cursor 144 and again aligns the cursor with the identified fiducial points $P_1, P_2$ and $P_3$. As the cursor is aligned with each point, the operator again signals the computer which records the coordinate of each fiducial point along axis $B_1$ of the second scout frame of reference. The operator then calls up the previously recorded first scout images $SC_{1C}$ and $SC_{1S}$ associated with the first image data set (FIGS. 4 and 5) and repeats the same cursor alignment process using the same fiducial points $P_1, P_2$ and $P_3$ on the patient's anatomy, so as to establish the locations of these fiducial points in coordinates $A_1, A_2$ and $A_3$ of the first frame of reference used for these scout images. The locations of fiducial points $P_1, P_2$ and $P_3$ in the first frame of reference $F_1$ and the second frame of reference $F_2$ define a transformation between the first frame of reference used in the first imaging procedure and the second frame of reference $B_1, B_2$ and $B_3$ used in the second imaging procedure. The transformation vector, including translation and rotations, between these two frames of reference is thus calculated by the control and reconstruction computer using known coordinate transformation algorithms. In a variant of this procedure, automatic pattern-matching algorithms may be employed to establish the locations of corresponding points in the two frames of reference and, thus, establish the transformation between the two frames of reference. In a further variant, the scout image data includes data for only one slice, in only a single plane. In this variant, it is assumed that points which are in registration along the axes lying in this plane will also be in registration along the axis normal to the plane of the scout image slice. In a further variant, preparatory to acquisition of the second image data set, the second the operator may instruct the apparatus to acquire a trial second scout image in the same nominal plane as the first scout image. The operator may evaluate the second scout image and determine visually if it appears to represent the same plane of the patient's anatomy as the earlier-acquired first scout image. If not, the operator instructs the apparatus to acquire another trial second scout image in another plane, preferably a plane parallel to the plane used in the last trial, and again compares it visually to the first scout image. Once a trial second scout image appears to match the first scout image the operator uses this trial scout image as a single second scout image to register the fiducial features. Here again, it is assumed that features registered in the plane of the first and second scout images will be in registration in directions perpendicular to such plane.

Figure 6:
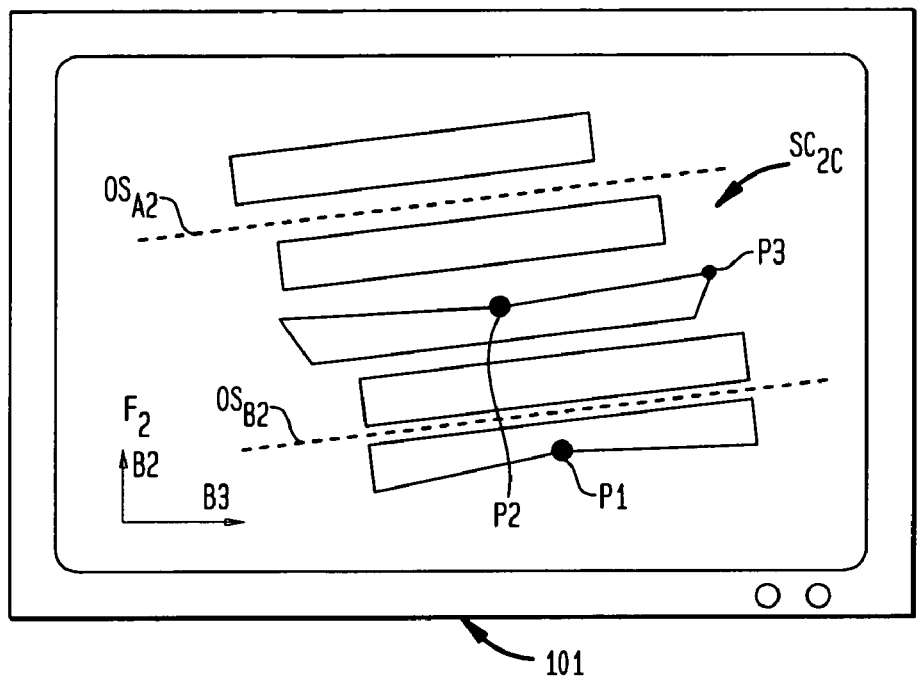
Figure 7:
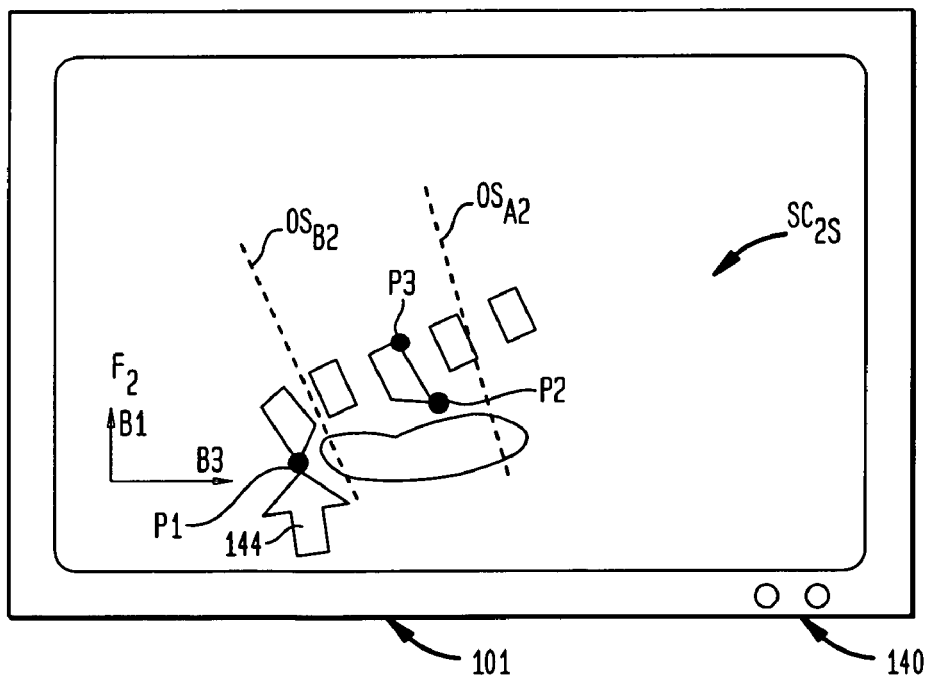

Once the transformation between the first and second frames of reference has been established, the computer transforms the data defining the position and orientation of the operative slices $OS_{A1}$, $OS_{B1}$ in the first frame of reference (FIGS. 4 and 5) into data defining corresponding slices $OS_{A2}$ and $OS_{B2}$ in the second frame of reference (FIGS. 6 and 7). The computer then actuates the other components of the system to acquire magnetic resonance data for voxels in these operative slices $OS_{A2}$ and $OS_{B2}$. These slices will lie at substantially the same position and orientation relative to the patient's body as the operative slices $OS_{A1}$ and $OS_{B1}$, acquired in the previous imaging procedure. The data relevant to the second operative slices is recorded in the same manner as discussed above, to provide a second image data set.

Figure 8:
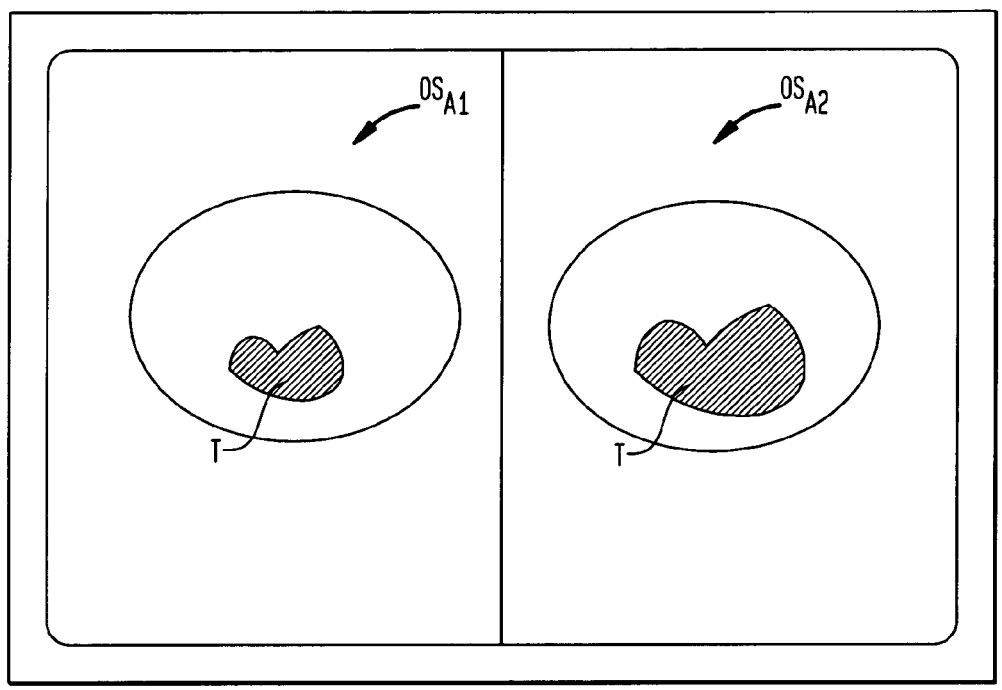

Once the second image data set has been recorded, the two data sets are compared with one another. In a simple comparison step, visually perceptible images of corresponding operative slices constructed from the first and second image data sets may be displayed side-by-side so that the physician may compare them visually. Such a comparison allows the physician to detect changes in the patient's anatomy occurring during the time between the first and second imaging procedures. For example, as seen in FIG. 8, side-by-side display of corresponding operative slices $OS_{A1}$ and $OS_{A2}$, acquired at different times, allows the physician to visually detect growth of a tumor T. This comparison is greatly facilitated by providing the two slices in substantially the same position and orientation relative to the patient's anatomy. Most preferably, the data constituting the two image data sets is acquired using substantially the same magnetic resonance parameters as, for example, the same static field strength and the pulse sequence parameters. Also, the image format parameters used to display the images desirably are the same. As used in this disclosure, the term "image format parameter" refers to a parameter which defines the transformation between recorded data and the visual properties of the image. For example, where the system displays a monochrome image, a pixel is displayed as white if the data for the corresponding voxel has a value above a certain threshold; as a light gray if the value in the corresponding voxel is within one range, as a darker gray if the voxel value is in another range, and so on. The image format parameters define these ranges.

In one arrangement, the image format parameters include a "window" defined by a value which will display as full white and another value which will display as full black. Desirably, the windows are the same in both images. Also, during display, the physician may adjust the image format parameters as, for example, by adjusting the window. Preferably, the computer is arranged to alter the image format parameters for both displayed images concurrently.

Methods according to this aspect of the invention can detect changes such as long-term growth or regression of normal or abnormal tissues occurring over periods of, for example, days, weeks, months or years. The same methods can also detect changes occurring over shorter times. For example, methods according to this aspect of the invention can be used to detect changes in the anatomy occurring over a few minutes following administration of a drug, radiant energy or other therapeutic agent. For example, some procedures for monitoring chemotherapy use invasive evaluation techniques as, for example, catheterization of the bladder, so that the physician can visually examine a bladder cancer. This catheterization typically is performed at relatively infrequent intervals because it is invasive and painful. Thus, in common protocols for monitoring the response of bladder cancer to chemotherapy, a chemotherapeutic agent is administered for six weeks and then the patient is catheterized to determine whether the tumor has shrunk or grown. Using the preferred techniques according to the present invention, however, the patient can be examined more frequently by magnetic resonance imaging as, for example, at intervals of a week or so. This more frequent examination can provide a faster indication as to whether the particular agent being administered is or is not effective, so that the physician can begin therapies if warranted. Moreover, magnetic resonance imaging can provide a more accurate indication as to the overall growth or shrinkage of the tumor than visual examination through a catheter. In a therapeutic monitoring method according to this preferred aspect of the invention, the second imaging step is performed after administration of a therapeutic agent such as an anti-tumor drug or radiation regimen and the step of comparing the images is performed so as to determine the presence or degree of response to the therapeutic regimen as, for example, by evaluating the size of a tumor, evaluating the appearance of a tumor such as its contrast to surrounding tissue, granularity or other characteristic. Preferably, the changes detected are real changes in the anatomy, as distinguished from temporary distortions of the anatomy induced by the cardiac or respiratory cycle. The term "non-cyclical" change is used herein to describe a real change in the anatomy, as distinguished from a distortion due to cardiac or respiratory cycling. Also, changes in the anatomy other than changes in the size or shape of particular tissues can be monitored. Thus, changes in metabolic or physiologic processes occurring within tissues which change the chemical nature of the tissue can be seen in magnetic resonance images and can be monitored using procedures according to this aspect of the invention.

Most preferably, the two sets of image data are compared automatically by the computer. To perform such a comparison, the two sets of image data must be in a common frame of reference. If the region of the patient imaged in the imaged data is a substantially rigid portion of the patient's anatomy, the registration achieved by registration of the scout images as discussed above will suffice to place all of the data for the operative slices of the second set in the same frame of reference as the operative slices of the first set. That is, a voxel having particular coordinates within the plane of slice $OS_{A2}$ in the second set theoretically lies at the same position within the patient as a voxel having the same coordinates in the corresponding slice $OS_{A1}$ of the first imaged data set. Alternatively, the data constituting the operative slices themselves may be used to register or be a part of the data constituting one data set with the corresponding data in another data set. This alternative procedure can be employed if the scout image registration steps discussed above are not used and can also be employed to provide more accurate registration for local areas within slices as discussed below even if the scout image registration steps are employed.

Figure 9:
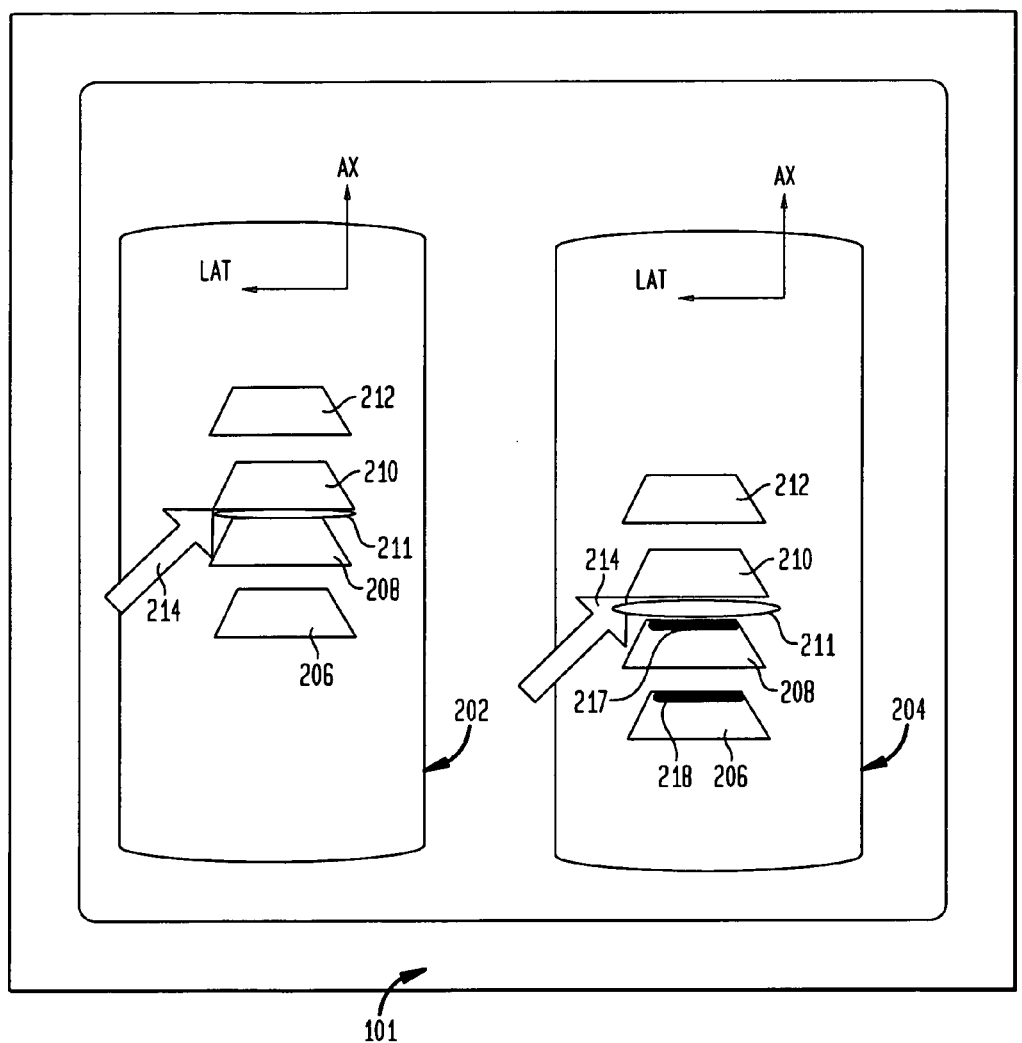

In one registration procedure using the operative slice data, the operator commands the system controller 126 to display on monitor 101 a visually-perceptible first image 202 (FIG. 9) reconstructed from a given operative slice, lying at a specified plane, the particular operative slices depicted in FIG. 9 are coronal slices, and hence each slice of the first data set depicts features disposed in a coronal plane at a given coordinate along the anterior-posterior axis of the patient in the first image data set. The operator also instructs the controller to display a visually perceptible second image 204 reconstructed from a slice in the second image. In the example illustrated, both images show coronal sections through the spine; a few vertebrae 206-212 are schematically depicted in each image. If the operator is not satisfied that both images show the same anatomical structures, and hence that both images represent sections through the patient at the same coronal plane, he can instruct the computer to select a new slice from one or both image data sets until he is satisfied that both images represent the same plane in the patient's anatomy. When he is satisfied, he signals the computer to accept the anterior-posterior ("AP") coordinates for both slices. At this point, the computer records the difference between the specified AP coordinates as the AP-direction offset between the coordinate systems. Next, the physician selects a common point on both images, as by moving a cursor 214 over the desired point in the first image 202 and actuating an input to indicate that the cursor is properly positioned. In the conventional manner, the computer tracks the location within the first image of the cursor as lateral ("LAT") and axial ("AX") coordinates in the frame of reference of the first image data set. When the physician actuates the input, the computer captures these coordinates as the LAT and AX coordinates of the selected point in the first frame of reference. When the physician positions the cursor over the same feature in the second image and actuates the input, the computer captures the LAT and AX coordinates of the same point in the second image frame of reference. Thus, the computer calculates the differences between the LAT coordinates in the two frames of reference and the differences between the AX coordinates in the two frames of reference, to obtain LAT and AX offsets between these frames of reference. The system can then register the two image data sets by adding the LAT offset to the LAT coordinate of each data point in the second data set and similarly adding the AX and AP offsets to these coordinates for each data point. More complex registration systems can be used. For example, the system can display sagital images in the AP-AX plane of each frame of reference in addition to the coronal images 202 and 204, and a similar cursor-positioning scheme can be used to capture the locations of three points on the same vertebra or other anatomical structure in all three dimensions in both frames of reference. From these locations, the system can calculate a combination of offsets along each axis and rotations about the axes required for registration, and can apply these to the data elements of one image data set using conventional image manipulation techniques to provide new coordinates for such data elements. In still further variations of the procedure, the registration step can be performed automatically, using known pattern-matching algorithms to find an anatomical structure in one image data set matching a structure designated by the physician in the other image data set using the cursor or other input device.

In the manual and automatic registration procedures discussed herein, fiducial markers can be used in place of anatomical features. Thus, fiducial markers can be physically attached to the patient's body prior to acquisition of the first image data set and remain in place during acquisition of the second image data set. The fiducial markers preferably are formed from a material which will provide contrast when seen against the background of the surrounding tissue in an MRI image. For example, the fiducial markers may be hollow objects filled with oil or other material having different magnetic resonance properties than the surrounding tissue, such as different spin-spin or spin-lattice relaxation time. Alternatively, the fiducial markers may be formed from a solid polymer or metal. The image data sets acquired during the procedure will include data representing the fiducial markers, and the displayed images will include depictions of the markers. In the cursor-based registration procedures discussed above, the operator may align the cursor with depictions of the fiducial markers, rather than with depictions of fiducial points in the anatomical structure. In an automated pattern-matching scheme, the pattern-matching algorithm may be arranged to search for data representing the known shapes of the fiducial markers. Also, if the fiducial markers have magnetic resonance properties differing from those occurring in other substances present in the imaging volume, the system may search through the image data set for data elements having those properties to locate the fiducial markers without use of pattern recognition.

Using the image data sets in a common frame of reference, and hence in registration with one another, the data in each data element of the second image data set is compared with the data in the data element of the first image data set having the same location. In a simple, single-element subtraction comparison scheme, the value specified by the data in each element of the second image data set may be subtracted from the value specified by the data in the corresponding element of the first image data set, or vice-versa. Other forms of comparison between such values may be used. For example, the value specified by the data in each element of the second image data set can be divided by the value specified by the data in the corresponding elements of the first image data set. Alternatively, the values specified by the data in the corresponding elements of the first and second data sets can be compared with one another so as to determine whether or not they are equal to one another within a preselected limit, and to provide a first result if they are equal and a second result if they are not. The result of the comparison is a comparison image data set representing the differences between the two images. In the subtraction scheme, the comparison image data set would have zero data at all locations if anatomical structures of the patient have not changed. In this scheme, non-zero values in elements of the comparison image data set indicate that a structure of the patient has changed between the time when the first image data set was acquired and the time the second image data set was acquired. In the thresholding scheme, each element of the comparison data set would contain either the first result or the second result. Elements having the second result would indicate a change in the anatomy.

In a variant of this approach, the elements of each data set may be combined into groups of plural data elements. For example, a plurality of first data elements having data representing magnetic resonance properties in a plurality of contiguous volume elements may be treated as a group. In effect, such a group forms a single, larger data element representing a single larger volume element. Alternatively, a plurality of first data elements representing a plurality of non-contiguous volume elements in a preselected spatial relationship to one another may be treated as a group. For example, a group of data elements representing volume elements disposed at a given radius from a central point, such as on a circle or sphere surrounding the central point, may be treated as a group. In a further variant, the group may also include the data element representing the volume element at the central point. The elements of any such group have data representing magnetic resonance characteristics in the neighborhood of a particular location. The data in the data elements of a plural-element group can be combined in various ways to provide one or more composite properties for the group. For example, the values represented by the data in the various elements can be summed or averaged. Also, a measure of the diversity among values represented by the various elements in the group as, for example, the standard deviation or range of such values, can be calculated. The elements of the second image data set can be combined into groups in the same manner, and a composite property can be calculated for each such group. The composite properties of each group of first data elements can be compared with the composite properties of the corresponding group of second data elements, representing the same location, in the same ways as the data in individual first data elements can be compared to the data in individual second data elements. Here again, the result is a comparison image data set, with a plurality of individual comparison data elements each having a value which represents the degree or existence of differences between data for the same location.

To minimize spurious data in the difference set, the comparison image data set can be subjected to an image processing procedure commonly referred to as "erosion" which removes non-zero data for particular voxels unless a certain number of neighboring voxels also have non-zero data.

The elements of the comparison image data set inherently have locations corresponding to the locations in the image data sets. Thus, a data element of the comparison data set derived by comparing data from voxels at a given location in two image data sets represents comparison data for the given location. The comparison data set thus may be displayed as one or more separate visual images. Alternatively or additionally, the comparison data set may be used to select regions within one or both image data sets corresponding to locations where differences exist as, for example, where the comparison image set has non-zero data or, more preferably, data which is of a magnitude greater than a specified threshold. The frame of reference of the comparison image data set is the same as the frame of reference of the first and second image data sets which have been registered with one another. Thus, a visually-perceptible image may be formed from either the first or second image data set and displayed. Those pixels corresponding to voxels where the comparison image data set has values above the specified threshold are highlighted in the display, as by displaying these pixels in a contrasting color, different intensity, flashing or other visually-perceptible indication. For example, the image 204 from the second data set may be displayed and pixels of the image representing voxels where changes have occurred between the two sets of image data may be shown darkened as seen at 217 in FIG. 9. This region of the image represents displacement of vertebra 208 relative to vertebra 210. Such displacement represents a meaningful anatomical change resulting, for example, from deterioration of a spinal laminae or "disk" 211 during the time between acquisition of the first and second data sets. The visible highlighting aids the physician in spotting subtle changes.

The highlighting procedure may also introduce artifacts into the displayed image. In the example depicted in FIG. 9, vertebra 206 has been displaced, relative to vertebra 210 along with vertebra 208; the space between vertebrae 206 and 208 is unaltered by any anatomical change in the vicinity of vertebra 206. Yet, vertebra 206 is displaced between the two images, so that highlighting 218 appears. To avoid this effect, the computer may suppress highlighting in regions of the displayed image more than a selected distance from the fiducial points used in the registration step as, in this example, more than a specified image from vertebra 210. The physician may designate fiducial points on a new anatomical structure such as vertebra 206 for registration using the same cursor-based input procedures discussed above, and the computer will re-register the image data sets in the same manner as discussed above to provide a new comparison data set, which can be used to highlight a displayed image in the same manner. The new comparison data set will show anatomical changes in the vicinity of the newly-designated structure on fiducial points. This procedure may be repeated numerous times using the same first and second image data sets, using different fiducial structures for registration in each repetition.

One particularly useful application of the techniques discussed above is in monitoring the growth or shrinkage of particular tissues, which may be abnormal tissues. In a further variant, the first and second image data sets are acquired using a magnetic resonance pulse sequence which yields tissue data for each voxel indicative of the presence or absence of a particular tissue characteristic within the voxel. The characteristic may be a characteristic indicative of an abnormality. For example, the data in each data element may include the value of spin-lattice relaxation time or $T_1$ for the tissue in such voxel. $T_1$ values above a threshold are indicative of malignancy. In this instance, the comparison data set can be combined with the $T_1$ values or tissue data to yield a revised comparison image data set indicating only those voxels where two conditions apply: (1) the difference between data values for the same voxel in the two image sets is above a set threshold; and (2) the $T_1$ value in a selected one of the first and second image data sets is above another threshold. The displayed visible image may be highlighted only at pixels corresponding to voxels of the revised comparison image data set. This procedure alerts the physician to the most critical anatomical information: where the malignancy is growing (or shrinking), in a simple and effective manner, which does not depend upon complex artificial-intelligence inferences. Similar techniques can be used with other abnormalities or with normal tissues of a specified type. For example, in monitoring development of a muscle in an athletic training program or physical rehabilitation, the signal characteristic may be a signal characteristic associated with muscle tissue. This characteristic can be combined with the difference between image data sets in the same way as the $T_1$ values discussed above to yield a revised comparison image data set indicating where changes in muscle tissue have occurred.

In the foregoing discussion, the individual being examined is referred to as a "patient." This does not imply that an individual being examined must be known or suspected to have a disease or abnormality. Thus, the word "patient" as used herein includes individuals who are not known or suspected to have any disease or abnormality, as well as those who have a known or suspected disease or abnormality. According to a further embodiment of the invention, the temporal comparison methods discussed above are applied as a screening technique to a series of patients having no known or suspected disease or abnormality. Thus, magnetic resonance image data sets are acquired from each patient at intervals of weeks, months or years. An image data set acquired at one time is automatically compared with an earlier image data set acquired from the same patient at a later time to provide a comparison image data set. In one embodiment, the first and second image data sets are $T_1$-weighted image data sets and, hence, the comparison image data set shows changes in the patient's body which may be indicative of a developing malignancy. Here again, one or more of the image data sets may be displayed as a visually-perceptible image. The comparison image data set itself may be displayed as a visually-perceptible image.

Techniques according to this aspect of the present invention are particularly useful in the case of screening procedures because they permit a human evaluator to focus on those aspects of the images which show some change. For example, a screening center may employ 100 slices per patient each time a patient is scanned. If such a center processes three patients per hour, it will generate data corresponding to 2400 visible images per day. The burden associated with reviewing all of these images may cause a reviewing radiologist to miss significant findings. However, where changes over time are highlighted, the radiologist can focus his or her attention on those images having highlighting. In a variant of the procedure discussed above, less than all of the data is displayed as visually perceptible images. If the automatic comparison between image data sets indicates a difference between successive data sets, the computer issues a difference signal. One or both of the data sets, most preferably the later-acquired data set involved in the comparison, is selected for inclusion in a subset of the generated data sets. By reviewing visually perceptible images in that subset, the radiologist will concentrate his or her review efforts on the data which is most likely to indicate development of an abnormality. Other factors may be considered in a scheme for deciding which data sets should be included in a subset to be reviewed by a human as, for example, the age of the patient, occupational data, medical history data, genetic data, or other data which tend to indicate the likelihood that the patient will develop an abnormality. In a variant of this approach, less than all of the data in some or all data sets is reproduced in the form of visible images for human inspection. For example, where the comparison step indicates a difference between data for particular corresponding slices in successive data sets from the same patient, only those slices, and optionally adjacent slices are displayed as visually perceptible images.

It is not essential to include the same number of slices in every data set. For example, in a screening procedure, a comprehensive base line data set incorporating data for numerous slices may be acquired during the first imaging procedure and subsequent data sets may include data for fewer slices. In a further variant, the automatic comparison step can be performed concomitantly with acquisition of a second or subsequent data set incorporating only a few slices. If comparison of this data with previously acquired data indicates that a difference exists, additional slices are acquired.

As mentioned above, use of the comparison data set in a visual display, either by display of the comparison image data set itself or by using the comparison data set to highlight a visually-perceptible image generated from another data set allows use of the comparative data without reliance on artificial intelligence or automated pattern recognition schemes. However, such schemes may be applied to the image data set. Merely by way of example, the system may find the dimensions of any region of contiguous voxels in the comparison image data set having non-zero values, or values above a selected threshold. Similarly, the comparison image data set can be processed to provide additional information. For example, the comparison image data set may be subjected to an automated feature-extraction process to find characteristics of the comparison image data set or of particular portions of the difference, features such as the ratio of dimensions can be found for each such region. These and other features can be extracted and compared with known disease patterns either in a rule-based system or by a neural network or other system capable of learning by exposure to a known learning set of comparison images.

To minimize or eliminate artifacts, the magnetic resonance pulse sequences may be gated to a particular time within the cardiac cycle, so that each repetition of the pulse sequence commences at the same phase of the cardiac cycle, as, for example, at a pre-selected time after end-systole or at a pre-selected time after end-diastole. The magnetic resonance pulse sequences also may be gated to the respiratory cycle, so that so that each repetition of the pulse sequence commences at the same phase of the respiratory cycle as, for example, at end-inspiration or end-expiration.

The disclosure of U.S. patent application Ser. No. 10/200,943, filed Jul. 23, 2002 is also incorporated by reference herein.

As these and other variations and combinations can be employed, the foregoing description of the preferred embodiments should be taken by way of illustration rather than by way of limitation of the invention as defined by the claims.

The invention claimed is:

1. A method of monitoring changes in a body of a patient over a prolonged period comprising the steps of:
   (a) imaging a part of a patient by magnetic resonance at a first time so as to provide a first image data set including a plurality of first data elements, each said first data element being associated with a location and having first data representing one or more characteristics of magnetic resonance signals from the location associated with the first data element;
   (b) imaging said part of said patient by magnetic resonance at a second time at least one day later than said first time so as to provide a second image data set including a plurality of second data elements, each said second data element being associated with a location and having second data representing one or more characteristics of magnetic resonance signals from the location which is associated with the second data element;
   (c) providing said first and second image data sets in a common frame of reference; and
   (d) comparing said first and second image data sets by comparing the first data in one or more groups of first data elements associated with particular locations to the second data in one or more groups of second data elements associated with the particular locations to derive a comparison image data set of body tissue structures of said patient
   wherein each said group of data elements includes a plurality of data elements and said step of comparing said groups of data elements includes deriving a composite property of each said group of first data elements from the data in all elements of that group, deriving a composite property of each said group of second data elements from the data in all elements of that group, and comparing the composite property of each group of first data elements with the composite property of the corresponding group of second data elements representing the same locations.

2. A method as claimed in claim 1 wherein said comparing step further includes converting said first and second image data sets into first and second visually-perceptible images, displaying said first and second images simultaneously and having a human observer visually compare the simultaneously-displayed images.

3. A method as claimed in claim 2 wherein said displaying step includes displaying said first and second images using identical image format parameters.

4. A method as claimed in claim 3 further comprising the steps of manually inputting at least one image format parameter, said displaying step including applying the manually-input image format parameter to both of said first and second images.

5. A method as claimed in claim 1 wherein both of said imaging steps are performed with said patient in substantially a same orientation relative to gravity.

6. A method as claimed in claim 1
wherein said imaging steps are performed so that said first and second data sets represent a common point in a cardiac cycle of the patient, a common point in a respiratory cycle, or both.

7. A method as claimed in claim 6 wherein each said group of data elements includes a plurality of data elements.

8. A method as claimed in claim 7 wherein each said group of data elements includes data elements representing one or more characteristics of magnetic resonance signals from a plurality of contiguous volume elements.

9. A method as claimed in claim 7 wherein each said group of data elements includes data elements representing one or more characteristics of magnetic resonance signals from a plurality of noncontiguous volume elements.

10. A method as claimed in claim 7 wherein each said group of data elements includes data elements representing one or more characteristics of magnetic resonance signals from a plurality of volume elements located at a same distance from a center point associated with such group of data elements.

11. A method as claimed in claim 1 wherein said imaging steps are performed so that said first image data set includes data for voxels in one or more operative slices and said second image data set includes data for voxels in one or more operative slices, the operative slices of said second image data set being disposed at a position and orientation relative to the body of the patient which is the same as a position relative to gravity of operative slices of the second data set.

12. A method as claimed in claim 11 wherein said second image data set includes data for fewer slices than said first image data set.

13. A method as claimed in claim 1 wherein said patient is a patient who does not have a known or suspected abnormality.

14. A method as claimed in claim 1 further comprising the step of subjecting said patient to a therapeutic regimen prior to said second imaging step, wherein said comparing step is performed so as to evaluate a presence or degree of response to said therapeutic regimen.

15. A method as claimed in claim 14 wherein said patient is a patient having a tumor and said therapeutic regimen is an anti-tumor regimen, said comparing step including evaluation of a tumor.

16. A method as claimed in claim 1 wherein each said group of data elements includes data elements representing one or more characteristics of magnetic resonance signals from a plurality of contiguous volume elements.

17. A method as claimed in claim 1 wherein each said group of data elements includes data elements representing one or more characteristics of magnetic resonance signals from a plurality of noncontiguous volume elements.

18. A method as claimed in claim 1 wherein each said group of data elements includes data elements representing one or more characteristics of magnetic resonance signals from a plurality of volume elements located at the same distance from a center point associated with such group of data elements.

19. A method as claimed in claim 1, further comprising displaying in a visually-perceptible image based at least in part on said comparison image data set.

20. A method as claimed in claim 19 wherein said displaying step includes the step of highlighting portions of said visually-perceptible image representing at least some regions of the body where said comparison image data indicates the presence of differences between said first and second image data sets.

21. A method as claimed in claim 19 wherein said patient is a patient who does not have a known or suspected abnormality.

22. A method of monitoring changes in a body of a patient comprising:
(a) in a first imaging step, imaging a part of a patient by magnetic resonance at a first time so as to provide a first image data set including a plurality of first data elements, each said first data element being associated with a location and having first data representing one or more characteristics of magnetic resonance signals from the location associated with the first data element;
(b) in a second imaging step, imaging said part of said patient by magnetic resonance at a second time later than said first time so as to provide a second image data set including a plurality of second data elements, each said second data element being associated with a location and having second data representing one or more characteristics of magnetic resonance signals from the location associated with the second data element;
(c) providing said first and second image data sets in a common frame of reference; and
(d) comparing said first and second image data sets so as to detect a non-cyclical change in body tissue structures represented by said first and second image data sets, the comparing step including comparing first data in groups of first data elements associated with particular locations to second data in groups of second data elements associated with the particular locations to derive a comparison image data set including a plurality of comparison data elements;
wherein said imaging steps are performed so that said first image data set includes data for voxels in one or more operative slices and said second image data set includes data for voxels in one or more operative slices, the operative slices of said second image data set being disposed at the same position and orientation relative to the body of the patient as the operative slices of the second data set;
and wherein:
said first imaging step includes the step of acquiring a first scout data set in a first frame of reference, said first scout data set including data defining a magnetic resonance image including a plurality of fiducial points on or in the body of the patient and recording slice-disposition data defining the position and orientation of the operative slices of the first image data set in said first frame of reference; and
said second imaging step includes the step of acquiring second scout data set in a second frame of reference, said second scout data set including data defining a magnetic resonance image including said fiducial points on or in the body of the patient, determining a transformation between said first and second frames of reference, and determining the position and orientation of operative slices for the second imaging step in said second frame of reference based on said slice-disposition data and said transformation so that the operative slices for the second imaging step will lie at the same position and orientation relative to said fiducial points as the operative slices for the first imaging step.

23. A method as claimed in claim 22 wherein said step of comparing said groups of data elements includes deriving a composite property of each said group of first data elements from data in all elements of each said group of first data elements, deriving a composite property of each said group of second data elements from data in all elements of each said group of second data elements, and comparing the composite property of each group of first data elements with the composite property of the corresponding group of second data elements representing the same locations.

24. A method as claimed in claim 22 wherein each said group of data elements consists of a single data element.

25. A method as claimed in claim 22, further comprising displaying a visually-perceptible image based at least in part on said comparison image data set.

26. A method as claimed in claim 25 wherein said displaying step includes a step of highlighting portions of said visually-perceptible image representing at least some regions of the body where said comparison image data indicates presence of differences between said first and second image data sets.

27. A method as claimed in claim 26 further comprising the step of acquiring tissue data in at least one of said magnetic resonance imaging steps indicative of the presence or absence of a predetermined characteristic in body tissues, wherein said highlighting step is performed so as to highlight portions of said visually-perceptible form representing at least some regions of the body where said tissue data indicates the presence of said predetermined characteristic and said comparison image data set indicates the presence of differences.

28. A method as claimed in claim 22 wherein each said scout data set includes data for voxels in two scout slices which are perpendicular to one another.

29. A method of monitoring changes in a body of a patient over a prolonged period comprising the steps of:

(a) imaging a part of a patient by magnetic resonance at a first time so as to provide a first image data set including a plurality of first data elements, each said first data element being associated with a location and having first data represent one or more characteristics of magnetic resonance signals from the location associated with the first data element;

(b) imaging said part of said patient by magnetic resonance at a second time at least one day later than said first time so as to provide a second image data set including a plurality of second data elements, each said second data element being associated with a location and having second data representing one or more characteristics of magnetic resonance signals from the location associated with the second data element;

(c) providing said first and second image data sets in a common frame of reference; and (d) comparing said first and second image data sets by comparing the first data in one or more groups of first data elements associated with particular locations to the second data in one or more groups of second data elements associated with the particular locations to derive a comparison image data set of body tissue structures of said patient; and (e) displaying a visually-perceptible image based at least in part on said comparison image data set, the displaying step including the step of highlighting portions of said visually-perceptible image, the method further comprising the step of acquiring tissue data in at least one of said magnetic resonance imaging steps indicative of presence or absence of a predetermined characteristic in body tissues and said highlighting step is performed so as to highlight portions of said visually-perceptible image representing at least some regions of the body where said tissue data indicates the presence of said predetermined characteristic and said comparison image data set indicates the presence of differences between said first and second image data sets.

30. A method as claimed in claim 29 wherein said imaging steps are performed with said patient in substantially a same orientation relative to gravity.

31. A method as claimed in claim 30 wherein said imaging steps are performed so that said first and second data sets represent a common point in a cardiac cycle of the patient, a common point in a respiratory cycle, or both.

* * * * *

UNITED STATES PATENT AND TRADEMARK OFFICE
CERTIFICATE OF CORRECTION

| | | |
|---|---|---|
| PATENT NO. | : 8,036,730 B1 | Page 1 of 1 |
| APPLICATION NO. | : 10/419407 | |
| DATED | : October 11, 2011 | |
| INVENTOR(S) | : Raymond V. Damadian and Anthony J. Giambalvo | |

It is certified that error appears in the above-identified patent and that said Letters Patent is hereby corrected as shown below:

On the Title Page:
Item (57) Abstract, lines 7-8, "locations a set" should read -- locations of a set --.

Column 2, line 60, "patient in an" should read -- patient is in an --.
Column 3, line 50, "system must" should read -- system, must --.
Column 6, line 27, "poles 56, extend" should read -- poles 56 extend --.
Column 7, line 22, "POSITIONAL" should read -- "POSITIONAL --.
Column 15, line 11, "variant, a the" should read -- variant, a --.
Column 16, line 33, "of an abnormality" should read -- of an abnormality. --.
Column 17, line 32, "is selected" should read -- are selected --.
Column 17, line 62, "data set" should read -- data set, --.
Column 20, line 67, "second scout" should read -- a second scout --.

Signed and Sealed this
Fourth Day of December, 2012

David J. Kappos
*Director of the United States Patent and Trademark Office*